United States Patent [19]
Sinkula

[11] 3,962,308
[45] June 8, 1976

[54] PROCESS FOR CONVERTING ESTERS TO AMINE SALTS

[75] Inventor: Anthony A. Sinkula, Kalamazoo, Mich.

[73] Assignee: The Upjohn Company, Kalamazoo, Mich.

[22] Filed: Aug. 28, 1974

[21] Appl. No.: 501,055

[52] U.S. Cl. .................... 260/465 D; 260/247.2 B; 260/268 R; 260/268 BQ; 260/268 H; 260/287 CP; 260/295 R; 260/295 AM; 260/295.5 R; 260/294.9; 260/326.8; 260/471 A; 260/501.11

[51] Int. Cl.$^2$ .............. C07D 215/48; C07D 213/75; C07C 101/44

[58] Field of Search ........ 260/287 R, 286 R, 295 R, 260/295 AM, 471 A, 294.9, 501.11, 465 D

[56] References Cited
OTHER PUBLICATIONS

Morrison and Boyd, "Organic Chemistry," 1967, p. 685.
Morrison et al., "Organic Chemistry," 1966, pp. 343–349.

*Primary Examiner*—Raymond V. Rush
*Assistant Examiner*—David E. Wheeler
*Attorney, Agent, or Firm*—Martin B. Barancik; Roman Saliwanchik

[57] ABSTRACT

A new method for converting certain diesters to physiologically acceptable amines which comprises reacting the diester with the desired amine in a solvent consisting essentially of water.

12 Claims, No Drawings

PROCESS FOR CONVERTING ESTERS TO AMINE SALTS

BRIEF DESCRIPTION OF THE PRIOR ART

The conventional means of forming an amine salt of an organic acid is to react the free acid with the salt forming amine base. Generally the free acid is prepared from the ester by alkaline hydrolysis to the metal salt which is then reacted with a mineral or organic acid to form the free organic acid.

It has now been discovered that certain types of organic esters can be converted in an essentially quantitative manner to the amine salts in a one-step reaction sequence.

BRIEF SUMMARY OF THE INVENTION

In accordance with this invention, there is now disclosed a process for converting esters to physiologically acceptable amine salts which comprises reacting an ester selected from the group consisting of

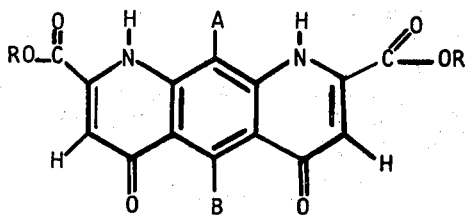

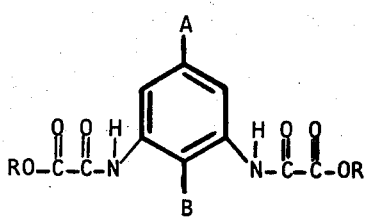

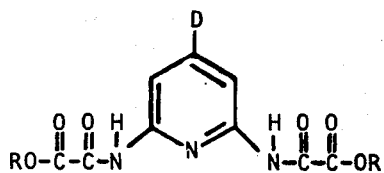

and

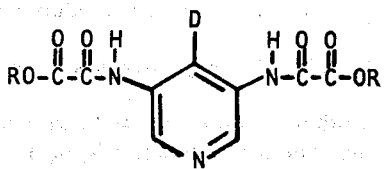

wherein R is selected from the group consisting of alkyl from one to six carbon atoms, inclusive, phenyl, and phenylalkyl wherein alkyl has one to four carbon atoms, inclusive; A and B are the same or different and are selected from the group consisting of hydrogen, alkyl of one to four carbon atoms, inclusive, phenyl, alkoxy of one to four carbon atoms, inclusive, halogen, trifluoromethyl, cyano, carboxy, and nitro; D is selected from the same group as A and B; with a physiologically acceptable amine in a solvent consisting essentially of water.

DETAILED DESCRIPTION OF THE INVENTION

The preferred esters of the above group are alkyl of one to four carbon atoms, inclusive, benzyl and phenethyl. The preferred A and B substituents are those selected from the group consisting of hydrogen, alkyl of one to four carbon atoms, inclusive, phenyl, alkoxy of one to four carbon atoms, inclusive, cyano, carboxy, nitro, fluoro and chloro. The preferred D group substituent is selected from the group consisting of hydrogen, alkyl of one to four carbon atoms, inclusive, phenyl, alkoxy of one to four carbon atoms, inclusive, cyano, carboxy, fluoro and chloro. The preferred physiologically acceptable amine is selected from the group consisting of tris(hydroxymethyl)aminomethane, ammonia, and adamantylamines.

As used in this specification, the phrase "alkyl of one to six carbon atoms, inclusive" includes methyl, ethyl, propyl, butyl, pentyl, hexyl, and isomers thereof. Illustrative examples of isomers are isopropyl, tert. butyl, neopentyl and isohexyl. Alkyl of a smaller number of carbon atoms has a similar scoping. The term "halogen" includes fluoro, chloro, bromo, and iodo.

The phrase "physiologically acceptable amine salt" refers to amines which are accepted by mammals in an essentially non-toxic manner when administered to mammals in conjunction with the acid moiety of the invention. Illustrative of the amines are those derived from primary, secondary or tertiary amines. Examples of suitable amines are methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, adamantylamines, and like aliphatic, cycloaliphatic, and araliphatic amines containing up to and including about eighteen carbon atoms as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-1-ethyl-1,3-propanediol, 2-amino-2-methyl-1-propanol, tris(hydroxymethyl)aminomethane, N-phenylethanolamine, N-(p-tert-amylphenyl)diethanolamine, galactamine, N-methylglucamine, N-methylglucosamine, ephedrine, phenylephrine, epinephrine, procaine, and the like. Also included within the amine scope are quaternary amines such as ammonium, tetramethylammonium, tetraethylammonium, benzyltrimethylammonium, phenyltriethylammonium, and the like.

The compounds prepared in accordance with this invention are useful in the prophylactic treatment of allergy of a reagin or non-reagin mediated nature, for example, extrinsic asthma, hayfever, urticaria, bird fancier's disease and intrinsic asthma.

The ester starting materials can be readily prepared by conventional methods from known reactants, for example, see U.S. Pat. No. 3,790,577 and U.S. Pat. No. 3,639,249.

The reaction occurs by simply contacting the ester with the desired amine. The environment in which the reaction takes place consists essentially of water. It is preferred to maintain the temperature of the reaction from about 20° to about 50° C., although temperatures of from about 15° to about 70° C. can be employed with facility. The reaction time is generally from about 12 to about 72 hours. The reaction time is somewhat dependent upon the completeness of reaction desired and the degree of reactant and product solubility in the water. A minimum of equal molar quantities of reactants can be employed. A molar excess of the amine up to about 5–10% can be employed to facilitate the reaction.

Through use of the invention disclosed herein, a simple one-step reaction sequence produces in essentially quantitative manner an amine salt which heretofore has been solely made through a three-step reaction sequence.

Following are specific examples in accordance with the invention. These examples are not meant to limit but merely to illustrate the inventive concept.

EXAMPLE 1

Di-tris(hydroxymethyl)methylammonium N,N'-(2,6-pyridinediyl)dioxamate

One gram ($3.23 \times 10^{-3}$ mole) of diethyl-N,N'-(2,6-pyridinediyl)dioxamate is suspended in 100 ml. of distilled water. 0.793 gram ($6.55 \times 10^{-3}$ mole) of tris(hydroxymethyl)aminomethane, hereafter referred to as THAM, is dissolved in 30 ml. of distilled water and this solution is added to the suspension of the dioxamate. The suspension is stirred until solution is complete. The water is removed in vacuo at 40° C.

Analysis Calcd. for: $C_{17}H_{29}N_5O_{12}$ C, 41.22; H, 5.90; N, 14.13. Found: C, 41.48; H, 6.00; N, 14.46.

EXAMPLE 2

Di-tris(hydroxymethyl)methylammonium-10-methyl-1,4,6,9-tetrahydro-4,6-dioxopyrido[3,2-g] quinoline-2,8-dicarboxylate Dimethyl 10-methyl-1,4,6,9-tetrahydro-4,6-dioxopyrido-[3,2-g] quinoline-2,8-dicarboxylate (1 Gm., $2.92 \times 10^{-3}$ mole) is suspended in 75 ml. of water and 0.71 Gm. ($5.84 \times 10^{-3}$ mole) of THAM, dissolved in 25 ml. of water, is added to this suspension. After stirring for 48 hours, the resulting yellow solution is filtered and the solvent removed in vacuo at 40° C. The residue is pulverized and dried in vacuo (50° C.), m.p. 211°–212° (decomp.)

Analysis Calcd. for: $C_{23}H_{32}N_4O_{12}$. C, 49.64; H, 5.80; N, 10.06. Found: C, 49.24; H, 6.00; N, 9.91.

EXAMPLE 3

Di-[tris(hydroxymethyl)methylammonium]-10-chloro-1,4,6,9-tetrahydro-4,6-dioxopyrido-[3,2-g]-quinoline-2,8-dicarboxylate Dimethyl-10-chloro-1,4,6,9-tetrahydro-4,6-dioxopyrido-[3,2-g] quinoline-2,8-dicarboxylate (1 Gm., $3.06 \times 10^{-3}$ mole) is suspended in 80 ml. of water and 0.75 Gm. ($6.12 \times 10^{-3}$ mole) of THAM, dissolved in 20 ml. of water, is added to this suspension. Solution occurs in about 15 minutes. The red-orange solution is heated at 50° C. for several hours while the color of the solution gradually changes to yellow. The filtered solution is warmed to 40° C. and the solvent removed in vacuo. The residue dried in vacuo has an indefinite m.p. (>236°).

Analysis Calcd. for: $C_{23}H_{29}N_4O_{12}Cl$ C, 45.80; H, 5.07; N, 9.71; Cl, 6.14. Found: C, 43.97; H, 5.35; N, 9.23; Cl, 5.79.

EXAMPLE 4

Di-[tris(hydroxymethyl)methylammonium]-N,N'-(2-chloro-m-phenylene)dioxamate

Diethyl-N,N-'(2-chloro-m-phenylene)dioxamate (1 Gm., $2.92 \times 10^{-3}$ mole) is suspended in 600 ml. of water. THAM (0.71 Gm., $5.86 \times 10^{-3}$ mole) is dissolved in 100 ml. of water and added to this suspension. The suspension is stirred. After 48 hours the colorless solution is filtered and the solvent removed in vacuo. The resulting crystals are dried in vacuo at 50° C., m.p. 167.2° – 174.5° C.

Analysis Calcd. for: $C_{18}H_{29}N_4O_{12}Cl$. C, 40.88; H, 5.53; N, 10.59; Cl, 6.70. Found: C, 40.71; H, 5.57; N, 10.61; Cl, 6.70.

EXAMPLE 5

Di-[tris(hydroxymethyl)methylammonium]-N,N'(2-chloro-5-cyano-m-phenylene)dioxamate Diethyl N,N'-(2-chloro-5-cyano-m-phenylene)-dioxamate (1 Gm., $2.72 \times 10^{-3}$ mole) is suspended in 75 ml. of water. THAM (0.66 Gm., $5.44 \times 10^{-3}$ mole) is dissolved in 25 ml. of water and added to the suspension. The suspension is warmed to 50° C. for 5 minutes and stirred for 48 hours. The resulting light orange solution is filtered and the solvent removed in vacuo. The residue is dried in vacuo at 50° C., m.p. 191.6° – 198.9°.

Analysis Calcd. for: $C_{19}H_{28}N_5O_{12}Cl$. C, 41.20; H, 5.10; N, 12.64; Cl, 6.40. Found: C, 41.63; H, 5.30; N, 12.58; Cl, 6.35.

EXAMPLE 6

In a manner similar to the procedure of Examples 1–5, the diethyl esters of the following compounds are converted to the THAM salt:

N,N'-(2-chloro-5-trifluoromethyl-m-phenylene)dioxamic acid,
N,N'-(5-cyano-m-phenylene)dioxamic acid,
N,N'-(5-nitro-m-phenylene)dioxamic acid,
N,N'-(5-carboxy-m-phenylene)dioxamic acid,
N,N'-(2-methyl-5-carboxy-m-phenylene)dioxamic acid,
N,N'-(2-chloro-5-carboxy-m-phenylene)dioxamic acid,
N,N'-(2-carboxy-m-phenylene)dioxamic acid,
N,N'-(5-methoxy-m-phenylene)dioxamic acid,
N,N'-(2-chloro-5-methyl-m-phenylene)dioxamic acid,
N,N'-(2-chloro-5-phenyl-m-phenylene)dioxamic acid,
the following substituted 1,4,6,9-tetrahydro-4,6-dioxopyrido 3,2-g -quinoline-2,8-dicarboxylic acid

| Position 5 | Position 10 |
| --- | --- |
| CH₃ | Cl |
| H | CN |
| H | COOH |
| CH₃ | CN |
| CH₃ | COOH |
| CF₃ | Cl |
| H | OCH₃ |
| H | F |

N,N'-(4-cyano-2,6-pyridinediyl)dioxamic acid,
N,N'-(4-cyano-3,5-pyridinediyl)dioxamic acid,
N,N'-(4-nitro-2,6-pyridinediyl)dioxamic acid,
N,N'-(4-nitro-3,5-pyridinediyl)dioxamic acid,
N,N'-(4-chloro-2,6-pyridinediyl)dioxamic acid,
N,N'-(4-chloro-3,5-pyridinediyl)dioxamic acid,
N,N'-(4-ethyl-2,6-pyridinediyl)dioxamic acid,
N,N'-(4-methyl-3,5-pyridinediyl)dioxamic acid,
N,N'-(4-methoxy-2,6-pyridinediyl)dioxamic acid,
N,N'-(4-ethoxy-3,5-pyridinediyl)dioxamic acid,
N,N'-(4-carboxy-2,6-pyridinediyl)dioxamic acid,
N,N'-(4-trifluoromethyl-3,5-pyridinediyl)dioxamic acid.

EXAMPLE 7

The following esters of each of the compounds exemplified in Examples 1 through 6 are converted to the THAM salt of the compound by the procedure of the invention.

R
methyl
isopropyl
butyl
pentyl
2,2-dimethylbutyl
phenyl
benzyl
phenethyl
α-α-dimethylbenzyl
4-(phenyl)butyl
α-α-dimethylphenethyl For example, dibutyl N,N'-(5-cyano-m-phenylene)-dioxamate is converted to the diTHAM salt. Dibenzyl N,N'-(2-chloro-5-trifluoromethyl-m-phenylene)dioxamate is converted to the diTHAM salt. Di-4-(phenyl)-butyl N,N'-(5-nitro-m-phenylene)dioxamate is converted to the diTHAM salt. Di-pentyl-1,4,6,9-tetrahydro-4,6-dioxopyrido[3,2-g]quinoline 2,8-dicarboxylate is converted to the diTHAM salt. Di-phenethyl N,N'-(4-chloro-2,6-pyridinediyl)dioxamate is converted to the diTHAM salt.

EXAMPLE 8

Each of the esters of Examples 1 through 7 is converted to the following illustrative di-amine salts by the procedure of the invention.
ammonia
diethylamine
morpholine
crotylamine
β-phenethylamine
2-methylpiperidine
2-amino-2-methyl-1-propanol
N-methylglucamine
ephedrine
tetramethylammonium For example, dihexyl N,N'-(2-chloro-5-cyano-m-phenylene)dioxamate is converted to the di(ethylamino)salt. Diphenethyl 10-chloro-1,4,6,9-tetrahydro-4,6-dioxopyrido[3,2-g]quinoline-2,8-dicarboxylate is converted to the di-N-methylglucamine salt. Di-butyl N,N'-(2,6-pyridinediyl)dioxamate is converted to the di-(2-amino-2-methyl-1-propanol) salt.

I claim:
1. A process for converting esters to physiologically acceptable amine salts which comprises the step of reacting an ester selected from the group consisting of

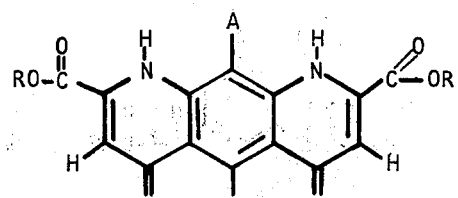

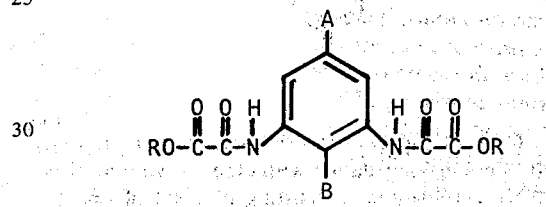

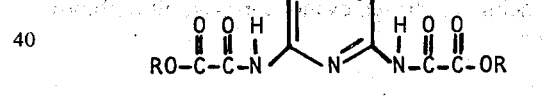

and

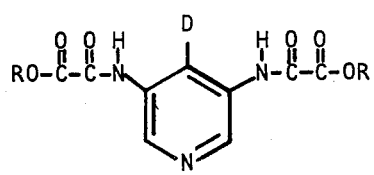

wherein R is selected from the group consisting of alkyl from one to six carbon atoms, inclusive, phenyl, and phenylalkyl wherein alkyl has one to four carbon atoms, inclusive; A and B are the same or different and are selected from the group consisting of hydrogen, alkyl of one to four carbon atoms, inclusive, phenyl, alkoxy of one to four carbon atoms, inclusive, halogen, trifluoromethyl, cyano, carboxy, and nitro with the proviso that neither A nor B is nitro in the pyrido[3,2-g]quinoline series; D is selected from the same group as A and B; with a physiologically acceptable amine in a solvent consisting essentially of water.

2. A process in accordance with claim 1 wherein the ester is selected from the group consisting of

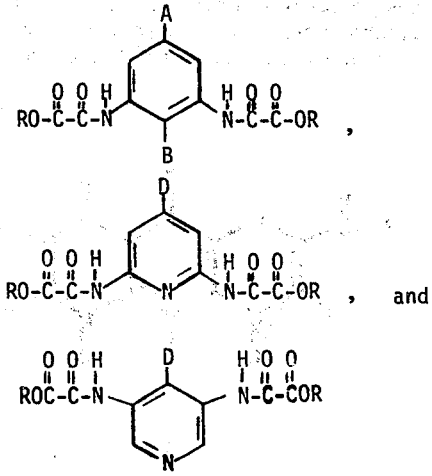

wherein R, A, B and D are as defined in claim 1.

3. A process in accordance with claim 1 wherein R is selected from the group consisting of alkyl of one to four carbon atoms, inclusive, benzyl and phenethyl.

4. A process in accordance with claim 1 wherein A and B are the same or different and are selected from the group consisting of hydrogen, alkyl of one to four carbon atoms, inclusive, alkoxy of one to four carbon atoms, inclusive, phenyl, cyano, carboxy, nitro, fluoro, and chloro.

5. A process in accordance with claim 1 wherein the physiologically acceptable amine is selected from the group consisting of tris(hydroxymethyl)aminomethane, ammonia, and adamantylamine.

6. A process in accordance with claim 1 wherein the compounds are the diesters of N,N'-(2-chloro-5-cyano-m-phenylene)dioxamic acid; N,N'-(2-chloro-5-phenyl-m-phenylene)dioxamic acid; N,N'-(2-chloro-5-trifluoromethyl-m-phenylene)dioxamic acid; N,N'-(5-cyano-m-phenylene)dioxamic acid; N,N'-(5-nitro-m-phenylene)dioxamic acid; 10-chloro-1,4,6,9-tetrahydro-4,6-dioxopyrido[3,2-g]dicarboxylic acid; N,N'-(2,6-pyridinediyl)dioxamic acid.

7. A process in accordance with claim 3 wherein the compounds are the diesters of N,N'-(2-chloro-5-cyano-m-phenylene)dioxamic acid; N,N'-(2-chloro-5-phenyl-m-phenylene)dioxamic acid; N,N'-(2-chloro-5-trifluoromethyl-m-phenylene)dioxamic acid; N,N'-(5-cyano-m-phenylene)dioxamic acid; N,N'-(5-nitro-m-phenylene)dioxamic acid; 10-chloro-1,4,6,9-tetrahydro-4,6-dioxopyrido[3,2-g]dicarboxylic acid; N,N'-(2,6-pyridinediyl)dioxamic acid.

8. A process in accordance with claim 1 wherein the compound is the diester of N,N'-(2-chloro-5-cyano-m-phenylene)dioxamic acid.

9. A process in accordance with claim 3 wherein the compound is the diester of N,N'-(2-chloro-5-cyano-m-phenylene)dioxamic acid.

10. A process in accordance with claim 5 wherein the compound is the diester of N,N'-(2-chloro-5-cyano-m-phenylene)dioxamic acid.

11. A process in accordance with claim 1 wherein the temperature of the reaction is from about 15° to about 70° C.

12. A process in accordance with claim 1 wherein D is selected from the group consisting of hydrogen, alkyl of one to four carbon atoms, inclusive, phenyl, alkoxy of one to four carbon atoms, inclusive, cyano, carboxy, fluoro, and chloro.

* * * * *